United States Patent
Neftel et al.

(10) Patent No.: US 10,722,634 B2
(45) Date of Patent: Jul. 28, 2020

(54) DIALYSIS DEVICE

(71) Applicants: GAMBRO LUNDIA AB, Lund (SE); DEBIOTECH S.A., Lausanne (CH)

(72) Inventors: Frédéric Neftel, Lausanne (CH); Pascal Bernard, Uccle (BE); Thomas Hertz, Lund (SE)

(73) Assignees: GAMBRO LUNDIA AB, Lund (SE); DEBIOTECH S.A., Lausanne (CH)

( * ) Notice: Subject to any disclaimer, the term of this patent is extended or adjusted under 35 U.S.C. 154(b) by 380 days.

(21) Appl. No.: 15/872,977

(22) Filed: Jan. 16, 2018

(65) Prior Publication Data

US 2018/0207339 A1    Jul. 26, 2018

Related U.S. Application Data

(63) Continuation of application No. 13/260,456, filed as application No. PCT/EP2010/053837 on Mar. 24, 2010, now abandoned.

(30) Foreign Application Priority Data

Mar. 24, 2019  (WO) .................. PCT/IB2009/051225

(51) Int. Cl.
| | |
|---|---|
| A61M 1/36 | (2006.01) |
| G16H 40/20 | (2018.01) |
| A61M 1/16 | (2006.01) |
| G06Q 50/22 | (2018.01) |
| G06F 19/00 | (2018.01) |
| G16H 20/17 | (2018.01) |
| A61M 1/28 | (2006.01) |

(52) U.S. Cl.
CPC ............ *A61M 1/16* (2013.01); *A61M 1/1613* (2014.02); *A61M 1/3609* (2014.02); *G06F 19/3481* (2013.01); *G06Q 50/22* (2013.01); *G16H 20/17* (2018.01); *A61M 1/28* (2013.01); *A61M 2205/3393* (2013.01); *A61M 2205/502* (2013.01); *A61M 2205/505* (2013.01); *A61M 2205/52* (2013.01)

(58) Field of Classification Search
CPC .... A61M 1/16; A61M 1/3609; A61M 1/1613; A61M 2205/502; A61M 2205/3393; A61M 1/28; A61M 2205/505; A61M 2205/52; G06F 19/3481; G16H 20/17; G16H 20/40; G16H 40/63; G16H 40/20; G06Q 50/22

See application file for complete search history.

(56) References Cited

U.S. PATENT DOCUMENTS

| | | | |
|---|---|---|---|
| 7,988,849 B2 * | 8/2011 | Biewer | A61M 1/28 210/94 |
| 2006/0195064 A1* | 8/2006 | Plahey | A61M 1/28 604/151 |
| 2007/0175827 A1* | 8/2007 | Wariar | G16H 20/40 210/645 |
| 2008/0033402 A1* | 2/2008 | Blomquist | G06F 19/3456 604/890.1 |

* cited by examiner

*Primary Examiner* — Eliza A Lam
(74) *Attorney, Agent, or Firm* — Nixon & Vanderhye P.C.

(57) ABSTRACT

A dialysis device comprising a prescriber interface and a programming means configured to allow, via the prescriber interface, input of a set of therapeutic objectives and a treatment plan and a re-evaluation means configured to, as a function of the therapeutic objectives and the treatment plan, suggest at least one treatment option comprising a set of settings of a treatment session to achieve said set of therapeutic objectives.

26 Claims, 2 Drawing Sheets

DIALYSIS DEVICE

CROSS REFERENCE TO RELATED APPLICATIONS

The present application is a continuation application of U.S. Ser. No. 13/260,456 that was filed on Sep. 26, 2011, which is a U.S. national stage application of International patent application PCT/EP2010/053837 filed on Mar. 24, 2010 designating the United States, and claims foreign priority to International patent application PCT/IB2009/051225 filed on Mar. 24, 2009, the contents of all three documents being herewith incorporated by reference in their entirety.

FIELD OF THE INVENTION

The present invention concerns the field of dialysis treatment. It relates more particularly to a dialysis device comprising an automated peritoneal dialysis machine or a hemodialysis machine that, based on input of certain data, is programmed to carry out a treatment session.

BACKGROUND OF THE INVENTION

Treatment of a patient with renal insufficiency is typically carried out according to a treatment plan created by a prescriber, such as a physician, based on certain therapeutic objectives. The treatment plan may comprise a schedule of treatment sessions and specific settings for each scheduled treatment session. The treatment plan typically also includes dietary advice, medications, frequency of blood samples for follow-up etc.

Treatment of renal insufficiency typically takes place in individual treatment sessions. One session may have duration between 1 and 12 hours.

Certain conditions may effect the actual execution of the treatment plan and the resulting treatment. One condition may be related to modifications of the treatment settings according to the wish of the patient. Such a modification may typically be the extension or shortening of duration of the treatment session. Another condition may be related to changes due to clinical conditions such as limited achievable blood flow, unexpectedly high weight gain, technical failure or a hypotensive episode. A further condition may be related to the actual result of a preceding treatment session.

A number of dialysis devices are known (see, for example, U.S. Pat. No. 5,326,476) in which the treatment parameters (duration, flow rate, etc.) are programmed by a prescriber such as a physician or a technician.

There are also devices (see, for example, U.S. Pat. No. 5,788,851) which are designed to allow a patient, or even a member of the patient's family assisting the patient, to interact with the programming of the treatment. In such devices, the interaction between patient and device is effected via an interface, for example implemented on a touch screen.

However, the devices provided with a patient interface, such as are described in the prior art, are not programmed in such a way as to define therapeutic or clinical objectives to be achieved, for example a predefined creatinine clearance value, a given dose defined as a Kt/V ratio where K=clearance of urea (ml/min), t=time on dialysis (min), V=volume of urea distribution in the body (ml), an individualized water removal target, a sodium balance.

Moreover, if treatment settings are modified by the patient, the devices of the prior art are limited to verifying the desired modification.

There is therefore a need to provide a dialysis device and a method where certain data inputs e.g. in the form of treatment session settings, results in at least one suggested treatment option securing that the therapeutic objectives initially fixed by the prescriber are achieved.

SUMMARY OF THE INVENTION

It is an object of the present invention to at least partly overcome one or more of the above identified limitations of prior art. Specifically it is an object to provide an improved dialysis device securing that a treatment objective is reached while allowing flexibility in the individual treatment sessions. This may be achieved by means of a dialysis device comprising a prescriber interface and a programming means configured to allow, via the prescriber interface, input of a set of therapeutic objectives and a treatment plan and a re-evaluation means configured to, as a function of the therapeutic objectives and the treatment plan, suggest at least one treatment option comprising a set of settings of a treatment session to achieve said set of therapeutic objectives.

The treatment plan defined by the prescriber is generally intended for a period or a number, n, of consecutive treatment sessions.

The set of settings comprises a number of individual settings wherein the individual setting may be duration of treatment session, blood flow, fluid removal rate, total removed fluid volume, dialysis fluid composition, dialysis fluid flow rate, dialysis fluid temperature, dialyzer type, treatment session schedule, number of exchanges per session, frequency of exchanges, fluid volume per exchange, duration of each dwell and glucose concentration in dialysis fluid.

An individual therapeutic or clinical parameter may be creatinine clearance, Kt/V ratio, ultrafiltration, sodium elimination, weight of the patient, total body water or blood pressure.

A treatment option would typically comprise a set of settings for a treatment session that together will result in reaching the therapeutic objectives.

In one embodiment of the invention the dialysis device comprises a patient interface and a modification means configured to allow, via the patient interface, modification of at least one of said settings wherein the re-evaluation means is configured to, as a function of the modified setting, suggest the at least one treatment option.

Various settings may be modified in accordance with the patient's wishes. The dialysis device is configured to suggest at least one treatment option including the modified setting(s) where one or several other settings of the session have been changed as a consequence of the setting(s) modified according to the patient's wishes. One setting modified by the patient may result in several suggested treatment options since a modification may be compensated for in several different ways.

In one embodiment of the invention the patient may modify settings during an ongoing treatment session. In this case as a consequence of the modifications, at least one treatment option may be offered at the consecutive session or sessions.

In one embodiment of the invention the dialysis device comprises a condition-determining means that is configured to measure clinical or therapeutic parameters wherein the re-evaluation means is configured to, as a function of the measured parameters during an on-going treatment session or measured parameters of at least one preceding treatment session, suggest the at least one treatment option. In another embodiment of the invention the re-evaluation means is configured to suggest the at least one treatment option as a function of the modified setting via the patient interface and the parameters measured by means of the condition-determining means.

According to a further embodiment of the invention the patient interface is configured to allow the patient to select one of the suggested treatment options whereby the dialysis device adjusts the settings in consequence of the selection to carry out the treatment session in accordance with the selected treatment option.

In one embodiment of the invention the patient interface is configured to display an indication of the result of the treatment in relation to the set of therapeutic objectives as measured by means of the condition-determining means. The result of the treatment in relation to the set of therapeutic objectives may be graphically displayed in the form of a graph, bar chart or an indicator gauge.

The main indication offered to the patient at the end of each treatment and/or at the start of programming may be a percentage attainment of the objectives, e.g. with a percentage figure of 85% signifying that the patient is in deficit by 15% relative to the therapeutic objectives thus visualizing adequacy of the treatment as a whole or each of the parameters indicative of the adequacy of the treatment.

In a further embodiment of the invention the programming means is configured to allow input, via the prescriber interface, limits of variation of each of the at least one setting that are allowed to be modified via the patient interface thereby allowing modification of each setting within these limits.

In one embodiment of the invention a modification of a setting may result in that the patient is advised to accept a certain treatment option rather than one of several options.

The programming means may also be configured to allow input, via the prescriber interface, of limits of variation of the measured clinical or therapeutic parameters. In one embodiment the dialysis machine comprises an alert means configured to issue an alert upon a deviation above or below a predefined limit of variation of a measured clinical or therapeutic parameter.

In a further embodiment of the invention the patient interface comprises a display configured to display the at least one suggested treatment option. The display means being functionally linked to the re-evaluation means.

In a further embodiment of the invention the patient interface and/or the prescriber interface is comprised by a graphical user interface. In one embodiment of the invention the graphical user interface is a touch screen.

In a further embodiment of the invention the dialysis device comprises a prescriber interface and a programming means configured to allow, via the prescriber interface, input of a set of therapeutic objectives and a treatment plan and a condition-determining means that is configured to measure clinical or therapeutic parameters during an ongoing or resulting from a treatment session wherein the patient interface is configured to display the result of the treatment in relation to the set of therapeutic objectives as measured by means of the condition-determining means.

In one embodiment of the invention, the patient is requested to respond to very specific clinical questions before modifying his treatment. Such responses may prevent the modification of said treatment. This set up may be referred to as a decision tree. The decision tree may also take into account information from recorded and/or measured parameters in order to better orient the patient and/or the treatment options as a function of the details gathered with the aid of these questions. The responses given by the patient will be communicated to the prescriber in the context of a medical monitoring of the patient after a reasonable time or, if appropriate, immediately, depending on the possible consequences on the state of health or therapeutic monitoring of the patient.

According to a first aspect of the invention the dialysis device comprises an automated peritoneal dialysis machine also referred to as a cycler. According to a second aspect of the invention the dialysis device comprises a hemodialysis machine.

The dialysis device according to the invention may be used advantageously in the context of home peritoneal dialysis and home hemodialysis respectively. In addition the dialysis device in the form of a hemodialysis machine may be used in a clinic or a self care setting.

DETAILED DISCLOSURE OF THE INVENTION

Below will be described the first and the second aspects of the invention, respectively, by way of illustrative examples.

First Aspect:

According to the first aspect of the invention where the dialysis device comprises an automated peritoneal dialysis machine, also referred to as a cycler, the dialysis treatment is performed by introducing dialysis fluid into the peritoneal cavity of a patient. The dialysis takes place over the peritoneum. After a period of time, typically 2 hours, the used dialysis fluid is drained from the peritoneal cavity and fresh dialysis fluid may be entered for continued treatment either directly or with a time delay. The dialysis fluid is usually available as a sterilized bagged fluid. For a treatment session during e.g. 8 hours multiple bags of fluid are used. The peritoneal dialysis machine in a cyclic manner assists in filling the peritoneum with fresh dialysis fluid from one bag at the time, possibly via a heater bag for heating the dialysis fluid to body temperature, and after a period of dwell draining the peritoneum and transferring the used dialysis fluid to a drain bag or to a drain.

By means of the dialysis device according to the present invention it is possible to provide for an optimized use of the available fluids as a function of the duration of the treatment session.

Example i

It is possible to reduce the duration of the dwell period in such a way as to ensure that the fluid from all bags is utilized during the available time for the treatment session while adhering to the intended number of fluid exchanges.

According to one embodiment of the invention various treatment settings may be modified by the patient. In addition to the duration of a treatment session, it is also possible to modify the total volume of the dialysis fluid during a treatment session, the dialysis fluid composition or the number of exchange cycles, where one exchange cycle comprises filling, dwell and drain of dialysis fluid originating from one bag.

In peritoneal dialysis, the therapeutic objectives to be reached over a period of n sessions may include one or more of the following: beta-2-microglobuline clearance, creatinine clearance, urea clearance, urea reduction ratio (URR), Kt/V ratio, sodium elimination, ultrafiltration volume, ultrafiltration rate, weight of the patient, blood chemistry parameters, haemoglobin and blood pressure. The blood chemistry parameters may include serum levels of phosphate, sodium, calcium, potassium, bicarbonate, albumin, urea or creatinine.

The at least one suggested treatment option for a period of n consecutive treatment sessions is advantageously adapted to the parameters measured during the preceding m treatment sessions. Such parameters may be measured by the condition-determining means e.g. in the form of an ultrafiltration measurement means, a patient scale, blood samples or a means for analysis of effluent (drained dialysis fluid). The patient's glucose level may also be monitored during the treatment session by means of the condition-determining means. It is also possible to measure the glucose level in the drained dialysis fluid.

According to one embodiment of the first aspect of the invention, the parameters measured during the preceding m treatment sessions include one or more of the following measurements: change in patient's weight, change in patient's blood pressure, change in patient's fat mass, quantity and nature of patient's food intake, quantity of water absorbed by patient, effective ultrafiltration, temperature of patient, physical strength of patient, residual renal function, urea removal, creatinine removal, change in blood parameters such as sodium, phosphate, calcium.

Example ii

The number n of consecutive peritoneal dialysis treatment sessions may be performed during a period lasting between 3 and 30 days, e.g. 7 days.

Example iii

The number m of preceding peritoneal dialysis treatment sessions may have been performed during a period lasting between 3 and 30 days, e.g. 7 days.

According to one embodiment of the invention, a compensation of a treatment result is achieved by requiring the patient, for a consecutive treatment session, to correct the effects of the preceding sessions, limiting the freedom of modification. In this case, the patient is preferably forced to choose from at least one of the following constraints: minimum duration of treatment, modification of the dialysis fluid composition or combination of dialysis fluid compositions, modification to the number of exchange cycles or to the exchange volume, modification of water intake between treatment sessions, addition of further exchange sessions during the day, or modification of the dialysis fluid composition used during these exchanges.

In one embodiment of the invention medical personnel responsible for the treatment of the patient is informed automatically by an alert when a deviation above or below a predefined limit is detected in relation to the therapeutic objectives that have been defined for the patient. The information may be transferred to the medical personnel remotely, for example by telephone or by Internet link.

Example iv

In case of peritoneal dialysis a deviation of ±30% over a 24-hour period may be accepted, provided that the weekly objective of, for example, 7 litres of ultrafiltration and 70 litres of creatinine clearance is achieved. The Kt/V objective may be 2.3.

The prescriber may take into account the filtration surface of the patient's membrane, its transport quality (high, medium or low), the residual renal function, and the body mass and clinical parameters such as weight, blood pressure and total body water when designing the treatment plan.

The prescriber in cooperation with the dialysis device configured for performing peritoneal dialysis defines the rules forming basis for the treatment options suggested by the re-evaluation means.

Example v

If the ultrafiltration falls below 700 ml on one day, a modification of the glucose or sodium concentration of the dialysis fluid and/or the addition of other colloidal osmotic pressure solutions during the treatment and/or the daily exchange or exchanges will be suggested as a treatment option by the reevaluation means. Alternatively, if the estimated clearance, on account of the reduced duration of the exchanges from 12 hours to 8 hours one night, drops by more than 30%, increase the number of exchanges the following night or prolong the duration of the treatment session from 10 hours to 13 hours, or else add supplementary daytime exchange sessions.

The patient may vary the duration of the treatment session from one day to another.

Example vi

As a function of the preceding sessions, the device may permit programming a duration of a treatment session of between 8 and 12 hours in normal time, or of between 10 and 14 hours if it registers a cumulative therapeutic deficit due to treatment sessions that are too short in the last few days, or of a minimum of 14 hours if this deficit is deemed to be too great, or may even propose a supplementary daytime treatment session. The other parameter on which the patient may act is the water/sodium intake and/or the ultrafiltration in case of weight gain. Such intake or ultrafiltration parameters may as well form part of a suggested treatment option.

Second Aspect:

According to the second aspect of the invention where the dialysis device comprises a hemodialysis machine the treatment may be carried out e.g. in a clinic where the patient is assisted by e.g. by a nurse, in a self care setting or at a patient's home. As disclosed above, the treatment of a patient with renal insufficiency is carried out according to a treatment plan created by a prescriber.

The therapeutic objectives for a hemodialysis treatment typically include dialysis dose per unit of time, the patients so called "dry weight" and target ranges for various blood parameters. The "dry weight" is the weight at which the patient should be at the end of the treatment, that is, after fluid removal. Blood parameters of importance may be blood pressure, hematocrit, serum phosphate, serum potassium, serum sodium etc. For each parameter, a target range is specified. The dialysis dose may be specified for each treatment, e.g. as URR (Urea Reduction Ratio) or spKt/V (Single Pool Kt/V) or similar, or for a longer time, e.g. weekly stdKt/V (Weekly Standard Kt/V).

The treatment schedule may be specified as one treatment session thrice weekly for a fixed period of time, typically 3-5 hours. Alternatively a treatment session may be scheduled every other day (i.e. 3.5 times per week), daily (i.e. 5-6 times per week, typically 2 hours) or during the night while sleeping, often referred to as nocturnal treatment (e.g. 3-6 times per week). The treatment schedule may be anything between these schedules, or a mix of two or more schedules, e.g. a mix of short daily and nocturnal treatments.

Settings defining each treatment session comprises e.g. dialyzer type, dialysis fluid composition, dialysis fluid temperature, dialysis fluid flow rate, target blood flow and treatment duration. Typically also the targeted weight loss is entered for each treatment session. The targeted weight loss is based on how much the patient weighs before treatment and knowledge of the prescribed dry weight.

In addition to prescribing a treatment schedule and settings for each treatment session, the prescriber may also set limits on allowed variation for each resulting setting. The limits are chosen by the prescriber to be safe for the patient, yet allow flexibility in how the individual dialysis treatment sessions are performed. For example, the prescriber may set a maximum allowed weight loss rate of 800 ml/min, to avoid hypotension which is a potentially dangerous condition.

Below are disclosed two exemplary treatment plans. In the exemplary treatment plans the target blood parameters and the dialysis fluid composition have been left out for simplicity. However, the parameters disclosed serves to illustrate the second aspect of the invention.

Treatment of patient A (daily dialysis e.g. performed in a home hemodialysis setting):
   Therapeutic objectives
      Dialysis dose: weekly stdKt/V=3.0
      Dry weight: 85 kg
   Treatment plan
      Treatment schedule
      6 times per week: Monday-Saturday
      Treatment session settings
      Dialyzer: Polyflux 170H
      Fluid flow: 500 ml/min
      Blood flow 350 ml/min
      Duration: 2.5 hours Treatment of patient B (thrice weekly dialysis e.g. performed as in-center hemodialysis, either self-care or assisted):
   Therapeutic objectives
      Dialysis dose: spKt/V 1.2
      Dry weight: 72 kg
   Treatment plan
      Treatment schedule
      3 times per week: Monday, Wednesday, Friday
      Treatment session settings
      Dialyzer: Polyflux 140H
      Fluid flow: 500 ml/min
      Blood flow 350 ml/min
      Duration: 5 hours The data representing the therapeutic objectives, the treatment plan (including schedule of treatments and session settings) and variation limits are entered into a programming means of the hemodialysis machine, via a prescriber interface. The prescriber interface may form part of the hemodialysis machine itself. Alternatively, the dialysis device comprises several parts such that the prescriber interface is separate from the dialysis machine itself.

Figure 1:
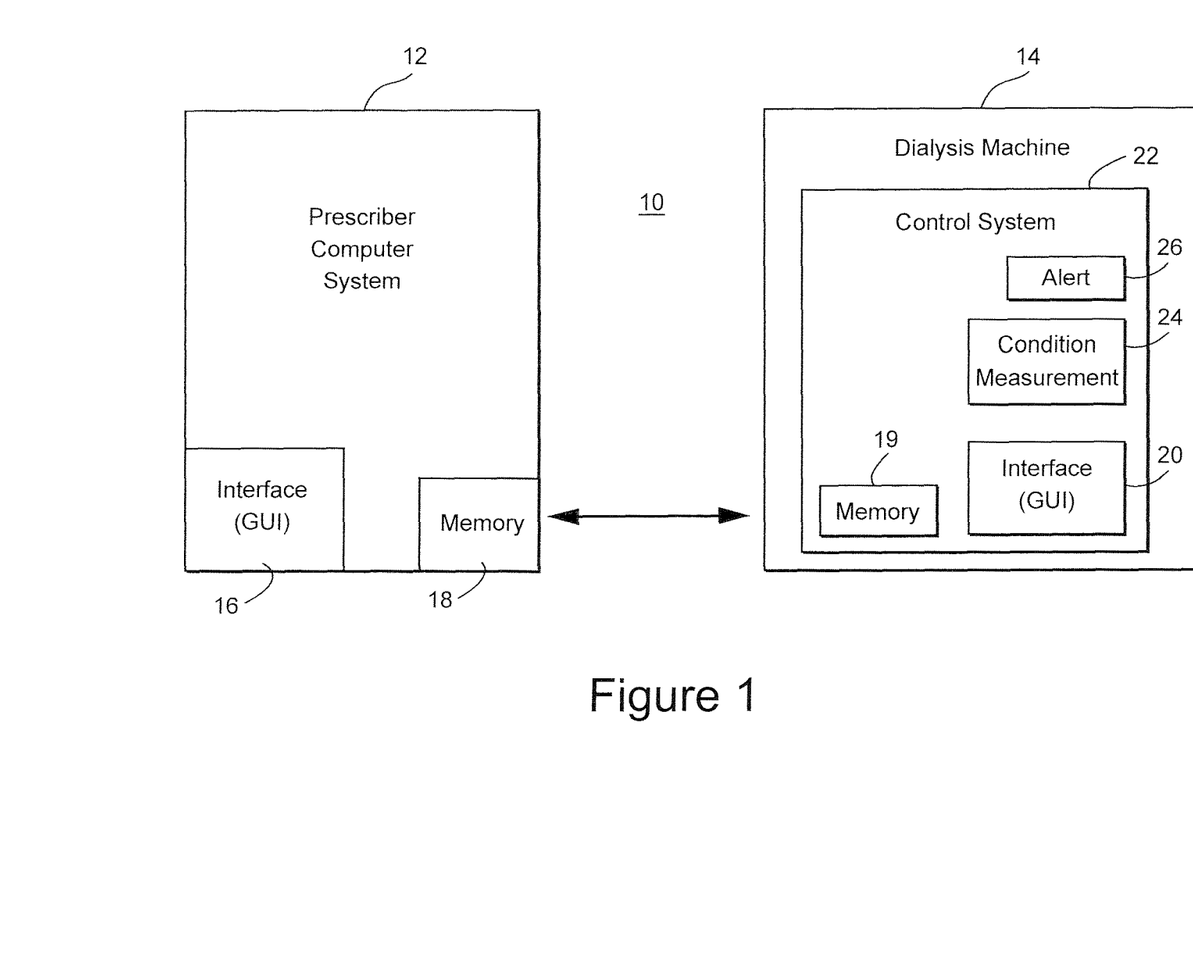
FIG. 1 is a schematic diagram of a computer system for prescribes to enter a treatment plan and a dialysis machine.
Figure 2:
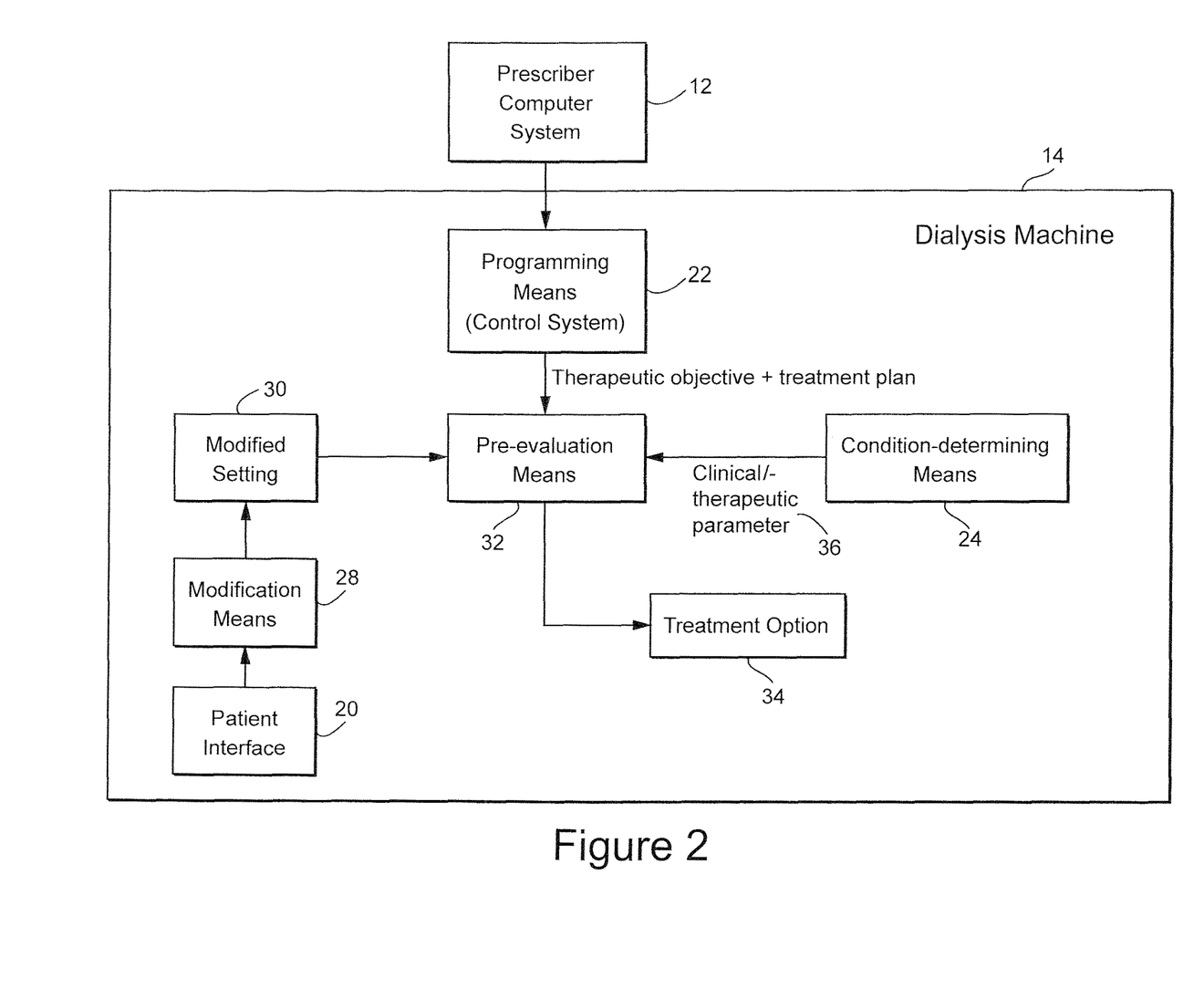
FIG. 2 is a schematic diagram of the methods and systems of the dialysis machine.

One embodiment of the second aspect of the invention is related to home hemodialysis where the patient treats himself at a home setting, possibly assisted by e.g. a family member. As shown in FIGS. 1 and 2, a home dialysis device 10 comprises two separate components; a computer system 12 at the clinic and the hemodialysis machine 14 in the patient's home. The computer system at the clinic comprises the prescriber interface 16, where the prescriber enters the treatment plan. The treatment plan may be electronically transferred to the hemodialysis machine, e.g. via a portable electronic media 18 such as a USB memory or via a direct electronic connection by telephone line or internet. Once the treatment plan is transferred to the hemodialysis machine the treatment may commence without further changes.

One embodiment of the second aspect of the invention is related to dialysis treatment performed in an in-center setting where the patient is assisted by a physician or a nurse. In the in-center clinic, each hemodialysis machine will serve several patients. The dialysis device for the in-center setting may comprise a single computer system for the whole clinic and several hemodialysis machines. The treatment plan for each patient is stored on the computer system until the patient to be treated has been assigned to a specific hemodialysis machine. The therapeutic objectives and/or the treatment plan may be transferred to the hemodialysis machine via an electronic network. Alternatively the therapeutic objectives and the treatment plan may be transferred to the hemodialysis machine from a personal portable memory device, such as a USB memory or an electronic patient card. Once the therapeutic objectives and/or the treatment plan is transferred to the hemodialysis machine the reevaluation means will suggest at least one treatment option and the treatment may commence without further changes once one of these options is selected via the patient interface.

According to one embodiment of the second aspect of the invention the patient interface 20 allows for modifications 28 of any of the resulting treatment settings. Reasonable modifications to the settings is allowed to be made via the patient interface 20, i.e. modifications are allowed as long as they are within limits set by the prescriber e.g. the duration of a treatment session may be set between 3 and 7 hours and it will not be possible to enter a duration of treatment session outside these limits.

Example I

Patient B according to the above exemplified treatment plan, may want to shorten the duration of the treatment session from 5 to 4 hours on a particular day. If this new duration of treatment is within the set limits the modification is allowed.

Based on a modified setting 30 the re-evaluation means 32 determines how other treatment settings may be changed to achieve the therapeutic objectives and suggests at least one treatment option. The re-evaluation means may also take into account other available data of the patient such as the treatment history and current treatment parameters when suggesting new treatment options 34 to achieve the therapeutic objectives.

Example II

Patient A according to the above exemplified treatment plan, has gained 3.0 kg since the last treatment session, a weight which has to be taken off to reach the therapeutic objective of the dry weight. The maximum allowed weight loss rate may have been set to 800 g/hour, in which case the maximum total weight loss that may be achieved in the prescribed 2.5 hour treatment is 2.0 kg. The re-evaluation means suggests a treatment option where the duration of the treatment is prolonged to 3 hours and 45 minutes, which allows the dry weight to be reached while maintaining a safe weight removal rate. The re-evaluation means may suggest a second treatment option, where a weight loss of only 2.0 kg in the current treatment session is reached, leaving a "debt" until the next treatment session.

Example III

During a treatment of Patient B, the maximum blood flow that may be achieved is 300 ml/min due to that the needles have been somewhat misplaced during cannulation. This is lower than the blood flow of 350 ml/min according to the entered treatment plan. Thus, the treatment dose (spKt/V=1.2) will not be reached as planned. The re-evaluation means suggests a treatment option showing an increase of the dialysis fluid flow rate from 500 to 800 ml/min. If increase of dialysis fluid flow is not sufficient to reach the treatment dose objective, additionally the re-evaluation means will suggest a treatment option where the treatment time is extended. Alternatively, the re-evaluation means may suggest a treatment option resulting in that a dose "debt" is left for the next treatment session or treatment sessions.

As exemplified above, there may be one or several options for the patient to choose from to reach the therapeutic objective.

In one embodiment of the invention the patient interface displays a list including at least one setting that may be modified.

Example IV

If Patient B in the example above decides that an extension of treatment time of 15 minutes is acceptable, then he/she sets the treatment time to be 5 hours and 15 minutes—and the re-evaluation means dynamically shows how high the dialysis fluid flow has to be to reach the treatment dose target. Once the user has decided that the suggested combination of parameters are acceptable, they are accepted via the patient interface and the hemodialysis machine dynamically makes the necessary adjustments.

In an alternative embodiment of the second aspect of the invention the hemodialysis machine comprises a condition-measuring means providing data so as to determine how well the therapeutic objectives are reached. Some therapeutic objectives are possible to measure or estimate e.g. the dialysis dose, which may be measured using blood samples analyzed for BUN (Blood Urea Nitrogen), or estimated using on-line clearance estimating technology. Thus, the re-evaluation means may take into account measurements conducted by the condition-measuring means 24 when suggesting treatment options to achieve the therapeutic objective of the treatment dose. Parameters 36 such as plasma phosphate content may be evaluated by means of blood samples in order to follow up how well therapeutic objectives on such parameters are achieved. Results of blood sample analysis is preferably entered into a treatment history record whereby the re-evaluation means may be configured to use the patient history data for suggesting consecutive treatment options.

In an alternative embodiment of the second aspect of the invention, the re-evaluation means takes into account the treatment history as well as several future treatment sessions when suggesting a treatment option, as will be described below. In addition to the treatment plan, this requires storing treatment history of each patient. In the home hemodialysis setting the treatment history may be stored in the memory 18 comprised by the control system 22 of the hemodialysis machine, since it is being used by a single patient. In the case of in-center dialysis, the treatment history of each patient has to be stored either on the clinic computer system (e.g. via network) or on a personal portable memory device. The data representing the patient history would typically include data related to previous treatment sessions (time and date, duration, blood flow or blood volume processed, fluid flow, dialysis fluid composition, weight loss, achieved online clearance etc) and possibly also indicators of therapeutic objectives (achieved dialysis dose, pre-dialysis weight, blood parameters such as pressure, haemoglobin, etc). The patient history to be taken into account typically comprises the treatment sessions during 7 preceding days.

Example V

If Patient A has a weight loss "debt" from an earlier treatment session, as suggested in the example above, the re-evaluation means would suggest a treatment option having longer treatment duration. If the weight loss debt is significant, the re-evaluation means may suggest a treatment option where the weight is removed over several future treatment sessions.

Example VI

If patient A has one or more treatment sessions with clearance efficiency below what is expected by the prescriber (e.g. due to reduced blood flow or reduced time), the re-evaluation means will suggest a treatment option at start of the next treatment session to achieve the targeted weekly dose of stdKt/V=3.0. This treatment option may comprise increasing dialysis fluid flow, increasing blood flow, increasing time or choosing a different dialyzer with a larger membrane surface area.

Example VII

If Patient A knows that he will have limited time for treatment tomorrow, he may choose to increase duration of the treatment session today, for example from 2.5 hours to 3.5 hours. This will increase the dialysis dose today and thus put him/her ahead of schedule in achieving the weekly dose target. The reevaluation means will then suggest a shorter time for the treatment tomorrow.

Examples VI and VII indicate that the patient may be below as well as above a therapeutic objective, in these examples the weekly dialysis dose target. The patient interface according to the invention therefore includes an indicator that in a simple and understandable fashion shows how well the therapeutic objectives are reached. This may be in the shape of a percentage figure, e.g. 85%, or a graphical representation such as a bar graph. The achievement of therapeutic objectives may also be shown over time, e.g. by a diagram with time on the horizontal axis. For example, if the therapeutic objective is the weekly dialysis dose, the graph may display the target as a horizontal line, and the actually achieved dose may be represented as connected points, where each point represents the achieved weekly dose over the last 7 days.

As stated above the dialysis device may comprise a condition-determining means 22 configured to measure parameters relevant for the therapeutic objective. The condition-determining means may comprise e.g. an online clearance estimating device, a blood pressure monitor, a blood composition analyser, a patient scale. The condition-determining means may be configured to detect failure to meet the therapeutic objectives and to issue an alert 26 to the patient (via the patient interface) and/or to the prescriber via e.g. telephone line or internet connection.

All of the steps, as well as any sub-sequence of steps, described above (comprising the first as well as the second aspect thereof) may be controlled by means of a programmed computer apparatus forming part of the dialysis device. Moreover, although the embodiments of the invention described above comprise computer apparatus and processes performed in computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the procedure according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc), an EPROM (Erasable Programmable Read-Only Memory), an EEPROM (Electrically Erasable Programmable ReadOnly Memory), or a magnetic recording medium, for example a floppy disc or a hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant procedures.

The term "comprises/comprising" when used in this specification is taken to specify the presence of stated features, integers, steps or components. However, the term does not preclude the presence or addition of one or more additional features, integers, steps or components or groups thereof.

The reference to prior art in this specification is not, and should not be taken as, an acknowledgment or any suggestion that the referenced prior art forms part of the common general knowledge in Australia, or in any other country.

The invention claimed is:

1. A dialysis device for performing a dialysis treatment based on a treatment plan to a patient, the dialysis device comprising:
   a patient interface configured to be positioned proximate to the patient and configured to receive input data from the patient; and
   a computer apparatus operatively connected to a memory device receiving the input data, the memory device storing a predetermined dialysis treatment plan for the patient, the dialysis treatment plan including a treatment schedule for a plurality of treatment sessions, each treatment session including a parameter on fluid flow and duration of the session,
   wherein the input data of the patient includes a modification request to the stored dialysis treatment plan to modify at least one of the treatment schedule and a parameter of a treatment session,
   wherein upon reception of the input data from the patient interface, the computer apparatus is configured to
   suggest to the patient and store to the memory device a plurality of modified dialysis treatment plans for the patient, each one of the plurality of modified dialysis treatment plans modifying the predetermined dialysis treatment plan but maintaining a therapeutic objective, the therapeutic objective including at least one of a prescribed value for a dry weight of the patient, a prescribed value for an ultrafiltration volume for the patient, and a prescribed value for a dialysis dose for the patient, and
   wherein upon presentation of the plurality of modified dialysis treatment plans to the patient, the patient interface is configured to
   permit the user to select one of the modified dialysis treatment plans for the patient.

2. The dialysis device according to claim 1, wherein the modification request of the patient includes a shortening of a duration of a treatment session, and in suggesting the plurality of modified dialysis treatment plans, the computer apparatus is configured to change at least one of a duration of other treatment sessions and the parameters of the dialysis treatment plan by simultaneously maintaining the prescribed value for the dialysis dose for the patient.

3. The dialysis device according to claim 1, wherein the modification request of the patient includes data on a weight gain of the patient, and in suggesting the plurality of modified dialysis treatment plans, the computer apparatus is configured to change a duration of at least one of the plurality of treatment sessions and the parameters of the dialysis treatment plan by simultaneously maintaining the therapeutic objective for the patient.

4. The dialysis device according to claim 1, wherein the modification request of the patient includes a lengthening of a duration of a treatment session, and in suggesting the plurality of modified dialysis treatment plans, the computer apparatus is configured to change at least one of a duration of other treatment sessions and the parameters of the dialysis treatment plan by simultaneously maintaining the prescribed value for the dialysis dose for the patient.

5. The dialysis device according to claim 1, further comprising:
   a measurement device configured to measure clinical or therapeutic parameters,
   wherein the suggestion of the plurality of modified dialysis treatment plans by the computer apparatus is based on the measured clinical or therapeutic parameters.

6. The dialysis device according to claim 1, further comprising:
   a measurement device configured to measure at least one of a glucose level and weight of the patient during a performance of the dialysis treatment plan,
   wherein the suggestion of the plurality of modified dialysis treatment plans by the computer apparatus is based on at least one of the measured glucose level and the measured weight of the patient.

7. The dialysis device according to claim 1, wherein the plurality of modified dialysis treatment plans are suggested such that the therapeutic objective is set to be reached over a number of treatment sessions, and
   wherein the suggestion of the plurality of modified dialysis treatment plans considers a treatment history and several future treatment sessions to allow a flexibility in the proposed plurality of modified dialysis treatment plans.

8. The dialysis device according to claim 1, wherein the patient interface is configured to permit the user to modify at least one of the following parameters: duration of a treatment session, blood flow, fluid removal rate, total removed fluid volume, dialysis fluid composition, dialysis fluid flow rate, dialysis fluid temperature, dialyzer type, treatment session schedule, number of exchanges per session, frequency of exchanges, fluid volume per exchange, duration of each dwell, and glucose concentration in dialysis fluid.

9. The dialysis device according to claim 1, wherein the therapeutic objective to be reached further includes at least one of the beta-2-microglobuline clearance, creatinine clearance, urea clearance, urea reduction ratio (URR), Kt/V ratio, sodium elimination, ultrafiltration rate, blood chemistry parameters, blood pressure, spKt/V (Single Pool Kt/V), and stdKt/V (Weekly Standard Kt/V).

10. A dialysis administering method for performing a dialysis treatment based on a treatment plan to a patient, the method comprising the steps of:
storing a predetermined dialysis treatment plan for the patient at a memory device of a computer apparatus, the dialysis treatment plan including a treatment schedule for a plurality of treatment sessions on the patient, each treatment session including a parameter on fluid flow and duration of the session;
receiving a modification request to the stored dialysis treatment plan of the patient via a patient interface, to modify at least one of the treatment schedule and a parameter of a treatment session,
suggesting to the patient and storing to the memory device a plurality of modified dialysis treatment plans for the patient by the computer apparatus, each one of the plurality of modified dialysis treatment plans modifying the predetermined dialysis treatment plan but maintaining a therapeutic objective, the therapeutic objective including at least one of a prescribed value for a dry weight of the patient, a prescribed value for an ultrafiltration volume for the patient, and a prescribed value for a dialysis dose for the patient, after the step of receiving; and
permitting the user to select one of the modified dialysis treatment plans for the patient for administering the dialysis solution, after the step of suggesting.

11. The dialysis administering method according to claim 10, wherein the modification request of the patient includes a shortening of a duration of a treatment session, and
in the step of suggesting the plurality of modified dialysis treatment plans, at least one of a duration of other treatment sessions and the parameters of the dialysis treatment plan are changed by simultaneously maintaining the prescribed value for the dialysis dose for the patient.

12. The dialysis administering method according to claim 10, wherein the modification request of the patient includes data on a weight gain of the patient, and
in the step of suggesting the plurality of modified dialysis treatment plans, at least one of a duration of at least one of the plurality of treatment sessions and the parameters of the dialysis treatment plan are changed by simultaneously maintaining the therapeutic objective for the patient.

13. The dialysis administering method according to claim 10, wherein the modification request of the patient includes a lengthening of a duration of a treatment session, and
in the step of suggesting the plurality of modified dialysis treatment plans, at least one of a duration of other treatment sessions and the parameters of the dialysis treatment plan are changed by simultaneously maintaining the prescribed value for the dialysis dose for the patient.

14. The dialysis administering method according to claim 10, further comprising:
measuring clinical or therapeutic parameters,
wherein the step of suggesting the plurality of modified dialysis treatment plans by the computer apparatus is based on the measured clinical or therapeutic parameters.

15. The dialysis administering method according to claim 10, further comprising:
measuring at least one of a glucose level and weight of the patient during a performance of the dialysis treatment plan,
wherein the step of suggesting the plurality of modified dialysis treatment plans by the computer apparatus is based on at least one of the measured glucose level and the measured weight of the patient.

16. The dialysis administering method according to claim 10, wherein the plurality of modified dialysis treatment plans are suggested such that the therapeutic objective is set to be reached over a number of treatment sessions, and
wherein the step of suggesting the plurality of modified dialysis treatment plans considers a treatment history and several future treatment sessions to allow a flexibility in the proposed plurality of modified dialysis treatment plans.

17. The dialysis administering method according to claim 10, wherein the patient interface is configured to permit the user to modify at least one of the following parameters: duration of a treatment session, blood flow, fluid removal rate, total removed fluid volume, dialysis fluid composition, dialysis fluid flow rate, dialysis fluid temperature, dialyzer type, treatment session schedule, number of exchanges per session, frequency of exchanges, fluid volume per exchange, duration of each dwell, and glucose concentration in dialysis fluid.

18. The dialysis administering method according to claim 10, wherein the therapeutic objective to be reached further includes at least one of the beta-2-microglobuline clearance, creatinine clearance, urea clearance, urea reduction ratio (URR), Kt/V ratio, sodium elimination, ultrafiltration rate, blood chemistry parameters, blood pressure, spKt/V (Single Pool Kt/V), and stdKt/V (Weekly Standard Kt/V).

19. A dialysis device for performing a dialysis treatment based on a treatment plan, the dialysis device comprising:
a user interface configured to be positioned proximate to the user and configured to receive input data from the user; and
a computer apparatus operatively connected to a memory device receiving the input data, the memory device storing a predetermined dialysis treatment plan defined by a prescriber and adapted to reach a therapeutic objective,
wherein the dialysis treatment plan including a treatment schedule for a plurality of treatment sessions, each treatment session including a parameter on fluid flow and duration of the session,
wherein the input data of the user includes a modification request to the predetermined dialysis treatment plan to modify at least one of the treatment schedule and a parameter of a treatment session,
wherein upon reception of the modification request from the user interface, the computer apparatus is configured to suggest to the user and store to the memory device a modified dialysis treatment plan, wherein the modified dialysis treatment plan is suggested such that the therapeutic objective is set to be reached over a number of treatment sessions, wherein the suggestion of the modified dialysis treatment plan takes into account at least one of a treatment history and future treatment sessions to allow a flexibility in the proposed modified dialysis treatment plan, and wherein upon suggestion of the modified dialysis treatment plan to the user, the dialysis device is configured to
carry out the treatment sessions in accordance with the modified dialysis treatment plan.

20. The dialysis device according to claim 19, wherein the modification request of the user includes a shortening of a duration of a treatment session, and in suggesting the modified dialysis treatment plan, the computer apparatus is configured to change at least one of the future treatment session and the parameters of the dialysis treatment plan by simultaneously maintaining the prescribed value for the dialysis dose.

21. The dialysis device according to claim 19, wherein the modification request of the user includes data on a weight gain of the user, and in suggesting the modified dialysis treatment plan, the computer apparatus is configured to change a duration of at least one of the plurality of future treatment sessions and the parameters of the dialysis treatment plan by simultaneously maintaining the therapeutic objective for the user.

22. The dialysis device according to claim 19, wherein the modification request of the user includes a lengthening of a duration of a treatment session, and in suggesting the modified dialysis treatment plan, the computer apparatus is configured to change at least one of a duration of the future treatment sessions and the parameters of the dialysis treatment plan by simultaneously maintaining the prescribed value for the dialysis dose.

23. The dialysis device according to claim 19, further comprising:
a measurement device configured to measure clinical or therapeutic parameters,
wherein the suggestion of the modified dialysis treatment plan by the computer apparatus is based on the measured clinical or therapeutic parameters.

24. The dialysis device according to claim 19, further comprising:
a measurement device configured to measure at least one of a glucose level and weight of the user during a performance of the dialysis treatment plan,
wherein the suggestion of the modified dialysis treatment plan by the computer apparatus is based on at least one of the measured glucose level and the measured weight of the user.

25. The dialysis device according to claim 19, wherein the user interface is configured to permit the user to modify at least one of the following parameters: duration of a treatment session, blood flow, fluid removal rate, total removed fluid volume, dialysis fluid composition, dialysis fluid flow rate, dialysis fluid temperature, dialyzer type, treatment session schedule, number of exchanges per session, frequency of exchanges, fluid volume per exchange, duration of each dwell, and glucose concentration in dialysis fluid.

26. The dialysis device according to claim 19, wherein the therapeutic objective to be reached includes a value for at least one of dry weight, ultrafiltration volume, dialysis dose, beta-2-microglobuline clearance, creatinine clearance, urea clearance, urea reduction ratio (URR), Kt/V ratio, sodium elimination, ultrafiltration rate, blood chemistry parameters, blood pressure, spKt/V (Single Pool Kt/V), and stdKt/V (Weekly Standard Kt/V).

* * * * *